(12) United States Patent
Sances Lopez

(10) Patent No.: US 9,572,313 B2
(45) Date of Patent: Feb. 21, 2017

(54) HYBRID PEPPER 'E20S1012777'

(71) Applicant: Enza Zaden Beheer B.V., Enkhuizen (NL)

(72) Inventor: Antonio Sances Lopez, Almeria (ES)

(73) Assignee: ENZA ZADEN BEHEER B.V., Enkhuizen (NL)

( * ) Notice: Subject to any disclaimer, the term of this patent is extended or adjusted under 35 U.S.C. 154(b) by 0 days.

(21) Appl. No.: 14/657,171

(22) Filed: Mar. 13, 2015

(65) Prior Publication Data

US 2015/0264877 A1 Sep. 24, 2015

Related U.S. Application Data

(60) Provisional application No. 61/955,047, filed on Mar. 18, 2014.

(51) Int. Cl.
*A01H 5/08* (2006.01)

(52) U.S. Cl.
CPC ........................................ *A01H 5/08* (2013.01)

(58) Field of Classification Search
None
See application file for complete search history.

(56) References Cited

U.S. PATENT DOCUMENTS

| | | |
|---|---|---|
| 5,262,316 A | 11/1993 | Engler et al. |
| 5,523,520 A | 6/1996 | Hunsperger et al. |
| 5,959,186 A | 9/1999 | Arevalos et al. |
| 6,124,528 A | 9/2000 | Shewmaker |
| 6,498,287 B2 | 12/2002 | Nash |
| 7,642,423 B2 | 1/2010 | Nicolet et al. |
| 8,013,222 B2 | 9/2011 | McCarthy |
| 8,026,424 B2 | 9/2011 | Van Der Heiden |
| 8,044,273 B2 | 10/2011 | Van Der Heiden |
| 8,067,681 B2 | 11/2011 | Van Der Heiden |
| 8,338,672 B2 | 12/2012 | Lindeman |
| 8,536,419 B2 | 9/2013 | Lindeman |
| 8,618,370 B2 | 12/2013 | Lindeman et al. |
| 8,816,170 B2 | 8/2014 | Aardse |
| 9,089,099 B2 | 7/2015 | Sances Lopez |
| 9,192,113 B2 | 11/2015 | Lindeman |
| 9,301,464 B2 | 4/2016 | Sances Lopez |
| 9,320,215 B2 | 4/2016 | Lindeman et al. |
| 9,474,220 B2 | 10/2016 | Van Der Heiden |
| 2006/0059585 A1 | 3/2006 | Jankowski et al. |
| 2006/0195921 A1 | 8/2006 | Van Der Heiden |
| 2009/0019561 A1 | 1/2009 | Van Der Heiden |
| 2009/0019599 A1 | 1/2009 | Van Der Heiden |
| 2009/0019600 A1 | 1/2009 | Van Der Heiden |
| 2009/0313713 A1 | 12/2009 | Lindeman |
| 2011/0197313 A1 | 8/2011 | Lindeman |
| 2012/0066797 A1 | 3/2012 | Lindeman et al. |
| 2013/0024962 A1 | 1/2013 | Aardse |
| 2014/0223611 A1 | 8/2014 | Lindeman et al. |
| 2014/0230084 A1 | 8/2014 | Sances Lopez |
| 2014/0259195 A1 | 9/2014 | Lindeman |
| 2014/0283167 A1 | 9/2014 | Sances Lopez |
| 2014/0289885 A1 | 9/2014 | Van Der et al. |
| 2015/0128320 P1 | 5/2015 | Lindeman |
| 2015/0327458 A1 | 11/2015 | Bouw |
| 2016/0302371 A1 | 10/2016 | Tarekegn |

FOREIGN PATENT DOCUMENTS

WO 01/62075 A2 8/2001

OTHER PUBLICATIONS

Advisory Action received for U.S. Appl. No. 10/552,969, mailed on Dec. 15, 2009, 3 pages.
Final Office Action received for U.S. Appl. No. 10/552,969 mailed on Apr. 7, 2014, 7 pages.
Final Office Action received for U.S. Appl. No. 10/552,969, mailed on Apr. 14, 2011, 11 pages.
Final Office Action received for U.S. Appl. No. 10/552,969, mailed on Sep. 8, 2009, 7 pages.
Non Final Office Action received for U.S. Appl. No. 10/552,969, mailed on Aug. 15, 2013, 12 pages.
Non Final Office Action received for U.S. Appl. No. 10/552,969, mailed on Apr. 15, 2008, 12 pages.
Non Final Office Action received for U.S. Appl. No. 10/552,969, mailed on Nov. 5, 2008, 10 pages.
Non Final Office Action received for U.S. Appl. No. 10/552,969, mailed on Oct. 7, 2010, 9 pages.
Restriction Requirement Received for U.S. Appl. No. 10/552,969, mailed on Jan. 8, 2008, 6 pages.
Final Office Action received for U.S. Appl. No. 11/776,008, mailed on Mar. 23, 2011, 8 pages.
Non Final Office Action received for U.S. Appl. No. 11/776,008, mailed on Nov. 9, 2010, 12 pages.
Notice of Allowance received for U.S. Appl. No. 11/776,008, mailed on Jun. 10, 2011, 6 pages.
Final Office Action received for U.S. Appl. No. 11/776,013, mailed on Mar. 23, 2011, 8 pages.
Non Final Office Action received for U.S. Appl. No. 11/776,013, mailed on Nov. 9, 2010, 12 pages.
Notice of Allowance received for U.S. Appl. No. 11/776,013, mailed on May 27, 2011, 7 pages.
Final Office Action received for U.S. Appl. No. 12/139,795, mailed on Sep. 26, 2011, 7 pages.
Non Final Office Action received for U.S. Appl. No. 12/139,795, mailed on Apr. 19, 2011, 14 pages.
Notice of Allowance received for U.S. Appl. No. 12/139,795, mailed on Jun. 24, 2013, 9 pages.
Notice of Allowance received for U.S. Appl. No. 12/704,229, mailed on Aug. 2, 2012, 8 pages.

(Continued)

*Primary Examiner* — David T Fox
(74) *Attorney, Agent, or Firm* — Morrison & Foerster LLP

(57) ABSTRACT

A hybrid pepper designated 'E20S1012777' is disclosed. The invention relates to the seeds of hybrid pepper 'E20S1012777' to the plants of hybrid pepper 'E20S1012777' and to methods for producing a hybrid plant, and to methods for producing other pepper lines, cultivars or hybrids derived from the hybrid pepper 'E20S1012777'.

12 Claims, No Drawings

(56) References Cited

OTHER PUBLICATIONS

Non-Final Office Action received for U.S. Appl. No. 13/189,237, mailed on Feb. 25, 2014, 11 pages.
Notice of Allowance received for U.S. Appl. No. 13/189,237, mailed on Jun. 3, 2014, 5 pages.
Final Office Action received for U.S. Appl. No. 13/232,466, mailed on Jun. 24, 2013, 10 pages.
Non-Final Office Action received for U.S. Appl. No. 13/232,466, mailed on Dec. 21, 2012, 13 pages.
Notice of Allowance received for U.S. Appl. No. 13/232,466, mailed on Aug. 28, 2013, 8 pages.
Notice of Allowance received for U.S. Appl. No. 13/232,466, mailed on Oct. 28, 2013, 3 pages.
Non-Final Office Action received for U.S. Appl. No. 13/766,219, mailed on Feb. 3, 2015, 12 pages.
Notice of Allowance received for U.S. Appl. No. 13/766,219, mailed on Jun. 5, 2015, 5 pages.
Non-Final Office Action received for U.S. Appl. No. 13/794,476, mailed on May 7, 2015, 12 pages.
Enza Zaden Beheer B.V., Database: Netherlands Applications for Plant Breeder's Rights, Application No. PPS1238 'E490264', Jan. 27, 2011, 2 pages (official copy only). See Statement Under 37 CFR § 1.98(a) (3).
Enza Zaden Beheer B.V., Official Gazette of the Community Plant Variety Office Jun. 2010; Publication Notice for Application No. CPVR 20101771 'Capsicum Annuum L.', Dec. 15, 2010, 3 pages (official copy only). See Statement Under 37 CFR § 1.98(a) (3).
Eshed et al., "Less-Than-Additive Epistatic Interactions of Quantitative Trait Loci in Tomato", Genetics, vol. 143, Aug. 1996, pp. 1807-1817.
Honma, S, "Capsicum Annuum Named Migold, PI 586678", Deposited 1986, 4 pages.
Jenkins, Merle, "The Segregation of Genes Affecting Yield of Grain in Maize", Journal of the American Society of Agronomy, vol. 21, 1940, pp. 55-63.
Kraft et al., "Linkage Disequilibrium and Fingerprinting in Sugar Beet", Theor. Appl. Genet., vol. 101, 2000, pp. 323-326.
Lefebvre et al., "The Capsanthin-Capsorubin Synthase Gene: A Candidate Gene for the Y Locus Controlling the Red Fruit Colour in Pepper", Plant Molecular Biology, vol. 36, 1998, pp. 785-789.
Molchova et al., "On the Interspecific Crossability Between *Capsicum annuum* L. and *Capsicum pubescens* R. & P.; *Capsicum annuum* L. and *Capsicum pendulum* Wild. (Sin Baccatum)", Capsicum Newsletter, vol. 1, 1982, pp. 39-41.
Newman et al., "Synthesis of Two Chromoplast-Specific Proteins During Fruit Development in Capsicum Annuum", Plant Physiology, vol. 91, 1989, pp. 455-458.
Nikova et al., "Overcoming of Interspecies Incompatibility in the Solanaceaous Genera Nicotiana and Capsicum via In Vitro Techniques", In Vitro Cellular and Developmental Biology, Animal, vol. 37, No. 3, Part 2, 2001, p. 40A.
Onus et al., "Monogenic Segregations in Backcross Progenies of Capsicum baccatum x Two Interspecific F1 Hybrids and Some Possible Explanations for Distorted Segregation Ratios in Capsicum", Turkish Journal of Botany, vol. 24, 2000, pp. 319-328.
Oren-Shamir et al., "Occurrence of the Chromoplast Protein ChrA Correlates with a Fruit-Color Gene in Capsicum Annum", Plant Molecular Biology, vol. 21, 1993, pp. 549-554.
Osuna-Garcia et al., "Endogenous Levels of Tocopherols and Ascorbic Acid during Fruit Ripening of New Mexican~Type Chile (*Capsicum annuunt* L.) Cultivars", Journal of Agricultural and Food Chemistry, vol. 46, No. 12, 1998, pp. 5093-5096.
Park et al., "Susceptibilization of Red Pepper *Capsicum-annuum* L. To Colletotrichum-Gloeosporioides Penz. in Relation to The Ripening of Fruits", Korean Journal of Plant Pathology, vol. 5, No. 3, 1989, pp. 262-270.
Poehlman et al., "Methods in Plant Breeding", In Breeding Field Crops, 4th ed., Iowa State University Press, 1995, pp. 172-174.
Quiros, Carlos F., "Solanacea: Pepper: *Capsicum* spp", VC 221, online fact sheet from www.plantsciences.ucdavis.edu/vc221/pepper, Apr. 2003, 3 pages.
Sahin et al., "Resistance in Capsicum pubescens to Xanthomonas campestris pv. vesicatoria Pepper Race 6", Plant Disease, vol. 82 No. 7, 1998, pp. 794-799.
Shifriss et al., "Studies of the Inheritance of Mature Fruit Color in *Capsicum annuum* L.", Euphytica, vol. 60, 1992, pp. 123-126.
Simpson et al., "Chromoplast Ultrastructure of Capsicum Carotenoid Mutants II. Effect of Light and CPTA", Z Pflanzenphysiol. Bd., vol. 83, 1977, pp. 309-325.
Smith, Paul G., "Inheritance of Brown and Green Mature Fruit Color in Peppers", Journal of Heredity, vol. 41, No. 5, 1950, pp. 138-140.
"Database WPI, Section Ch, Week 20327", Derwent Publications Ltd., Antal, J., 'Kurtovszka Kapia' Capsicum annum, Jan. 28, 2003, 1 page.
Zijlstra et al., "Pollen Tube Growth in Interspecific Crosses between *Capsicum* Species", HortScience, vol. 26, No. 5, 1991, pp. 585-586.
CPVR 2009/2170. Sweet46. Filed Oct. 23, 2009. Granted Apr. 23, 2012, 7 pages.
NL PBR PPS1165. Sweet46. Filed Oct. 23, 2009. Granted Jan. 27, 2012, 7 pages.
Non-Final Office Action received for U.S. Appl. No. 14/091,275, mailed on Oct. 15, 2015, 6 pages.
Non-Final Office Action received for U.S. Appl. No. 14/211,892, mailed on Oct. 7, 2015, 13 pages.
Notice of Allowance received for U.S. Appl. No. 13/794,476, mailed on Aug. 3, 2015, 5 pages.
Bouw, Elbert, Unpublished U.S. Appl. No. 14/714,016, filed May 15, 2015, titled "Hybrid Pepper E20C0043", 43 pages.
Non Final Office Action Received for U.S. Appl. No. 14/300,129, mailed on Jan. 26, 2016, 13 pages.
Unpublished U.S. Appl. No. 12/961,222, filed Dec. 6, 2010.
"Carmen Italian Sweet Pepper", uploaded from Bonnie Plants website, 2006, 1 page.
"Pepper Capsicum Annum Marconi Red", uploaded from davesgarden.com, 2013, 1 page.
Non Final Office Action received for U.S. Appl. No. 14/121,903, mailed on May 19, 2016, 9 pages.

HYBRID PEPPER 'E20S1012777'

CROSS-REFERENCE TO RELATED APPLICATIONS

This application claims the benefit of U.S. Provisional Application No. 61/955,047, filed Mar. 18, 2014, which is hereby incorporated by reference in its entirety.

FIELD OF THE INVENTION

The present invention relates to the field of plant breeding. In particular, the present invention relates to a new and distinctive pepper (*Capsicum annuum*) hybrid designated 'E20S1012777'.

BACKGROUND OF THE INVENTION

The bell pepper (*Capsicum annuum*) originated in Mexico and the neighboring areas of Central America. Soon after Columbus' discovery of this plant, it was grown worldwide and used as a spice and a medicine. Today, pepper plants can be found growing wild in tropical areas around the world. Many countries grow it as a crop. Many of the hot peppers can be found in Latin America and China, but the United States prefers bell peppers. Peppers are used for fresh consumption, and they are processed into powders, sauces, and salsas. Many of the new cultivars grown today can be traced back to the early plants.

The genus *Capsicum* and species *annuum* includes most of the peppers grown in the United States. These can be further grouped into two broad categories: chile peppers which are pungent (hot) and sweet peppers which are non-pungent (mild). The United States produces four percent of the world's *capsicum* peppers (sweet and hot), ranking sixth behind China, Mexico, Turkey, Spain and Nigeria. Bell peppers are the most common sweet pepper and are found in virtually every retail produce department. Grown commercially in most states, the U.S. industry is largely concentrated in California and Florida, which together accounted for 78% of output in 2000. New Jersey, Georgia, and North Carolina round out the top five producing states (Economic Research Service, USDA, Vegetables and Melons Outlook/VGS-288/Dec. 14, 2001).

Bell peppers are eaten raw, cooked, immature and mature. Often nutritional content is altered by the changes in the way they are consumed. Per capita consumption of bell peppers in 1995 was 6.2 pounds. They are an excellent source of Vitamin C, Vitamin A, and Calcium. Red peppers have more of these qualities than the immature green peppers.

Peppers grown in temperate regions are herbaceous annuals, but are herbaceous perennials where temperatures do not drop below freezing. Pepper plants' growth habit may be prostrate, compact, or erect, but it is determinate in that after it produces nine to eleven leaves a single stem terminates in flowers. These plants are grown for the edible fleshy fruit produced by this dichotomous growth. Peppers are non-climacteric which means they do not produce ethylene. They need to stay on the vine to continue the ripening process. A deep taproot will form if the plant root system is uninjured during transplanting. The spindle root will develop fibrous secondary root systems spreading laterally and downward. On the soil surface the stem will produce adventitious roots, but not as easily as tomatoes. The leaves of the pepper plant arise singly and are simple, entire, and asymmetrical. Typical of all Solanaceous plants, the leaves are arranged alternately on the stem. They are shiny and glabrous and vary in shape from broadly ovate to ovate lanceolate. The flowers develop singly or in twos or threes continuously as the upper structure of the plant proliferates. The corolla is white and five lobed while the anthers are bluish or yellowish in color. The flowers have an open anther formation and will indefinitely self-pollinate. They are also pollinated by insects, which increases the chances of cross-pollination. Unlike tomatoes, whose pollen becomes nonviable in high temperatures, the pepper flowers' pollen is not extremely heat sensitive and it remains viable up to 100° Fahrenheit producing fruit throughout the season.

The fruit of a pepper plant is classified as a berry with colors from green, yellow, red, purple, black, brown, white, and orange. Green is an immature fruit, yet commonly eaten this way, and as the fruit matures it changes color. In most commercial cultivars color changes are from green to red, green to yellow or green to orange. Usually, fruits of the purple and white varieties have these colors as they develop, and therefore do not have a green stage. For fruit to set, the ovaries need to be fertilized. Auxin is then produced by the seeds, which determine fruit cell elongation. The number of seeds fertilized will determine the size and shape of the fruit. The seed develop on the interior and attach to the veins. Fully developed seed is kidney shaped. There are about 4,500 seeds per ounce.

Pepper is an important and valuable field crop. Thus, there is a continued need for new hybrid peppers.

SUMMARY OF THE INVENTION

In order to meet these needs, the present invention is directed to improved hybrid peppers. In one embodiment, the present invention is directed to a hybrid pepper, *Capsicum annuum*, seed designated as 'E20S1012777' having NCIMB Accession Number 142587. In one embodiment, the present invention is directed to a *Capsicum annuum* pepper plant and parts isolated therefrom produced by growing 'E20S1012777' pepper seed. In another embodiment, the present invention is directed to a *Capsicum annuum* plant and parts isolated therefrom having all the physiological and morphological characteristics of a *Capsicum annuum* plant produced by growing 'E20S1012777' pepper seed having NCIMB Accession Number 42587. In still another embodiment, the present invention is directed to an $F_1$ hybrid *Capsicum annuum* pepper seed, plants grown from the seed, and fruit isolated therefrom having 'E20S1012777' as a parent, where 'E20S1012777' is grown from 'E20S1012777' pepper seed having NCIMB Accession Number 42587.

Pepper plant parts include pepper leaves, ovules, pollen, seeds, pepper fruits, parts of pepper fruits, flowers, cells, and the like. In another embodiment, the present invention is further directed to pepper leaves, ovules, pollen, seeds, pepper fruits, parts of pepper fruits, and/or flowers isolated from 'E20S1012777' pepper plants. In certain embodiments, the present invention is further directed to pollen or ovules isolated from 'E20S1012777' pepper plants. In another embodiment, the present invention is further directed to protoplasts produced from 'E20S1012777' pepper plants. In another embodiment, the present invention is further directed to tissue culture of 'E20S1012777' pepper plants, and to pepper plants regenerated from the tissue culture, where the plant has all of the morphological and physiological characteristics of 'E20S1012777' pepper. In certain embodiments, tissue culture of 'E20S1012777' pepper plants is produced from a plant part selected from leaf, anther, pistil, stem, petiole, root, root tip, fruit, seed, flower, cotyledon, hypocotyl, embryo and meristematic cell.

In yet another embodiment, the present invention is further directed to a method of selecting pepper plants, by a) growing 'E20S1012777' pepper plants where the 'E20S1012777' plants are grown from pepper seed having NCIMB Accession Number 42587 and b) selecting a plant from step a). In another embodiment, the present invention is further directed to pepper plants, plant parts and seeds produced by the pepper plants where the pepper plants are isolated by the selection method of the invention In another embodiment, the present invention is further directed to a method of making pepper seeds by crossing a pepper plant grown from 'E20S1012777' pepper seed having NCIMB Accession Number 42587 with another pepper plant, and harvesting seed therefrom. In still another embodiment, the present invention is further directed to pepper plants, pepper parts from the pepper plants, and seeds produced therefrom where the pepper plant is grown from seed produced by the method of making pepper seed of the invention. In some embodiments, the pepper plant grown from pepper seed produced by the method of making pepper seed is a transgenic pepper plant.

In another embodiment, the present invention is further directed to a method of making pepper variety 'E20S1012777' by selecting seeds from the cross of one 'E20S1012777' plant with another 'E20S1012777' plant, a sample of 'E20S1012777' pepper seed having been deposited under NCIMB Accession Number 42587.

According to the invention, there is provided a hybrid pepper plant designated 'E20S1012777'. This invention thus relates to the seeds of hybrid pepper 'E20S1012777', to the plants of pepper 'E20S1012777' and to methods for producing a pepper plant produced by crossing hybrid pepper 'E20S1012777' with itself or another pepper plant, and to methods for producing a pepper plant containing in its genetic material one or more transgenes and to the transgenic pepper plants produced by that method. This invention also relates to methods for producing other pepper cultivars or hybrids derived from hybrid pepper 'E20S1012777' and to the pepper cultivars and hybrids derived by the use of those methods. This invention further relates to pepper seeds and plants produced by crossing hybrid pepper 'E20S1012777' with another pepper cultivar.

In another embodiment, the present invention is directed to methods for producing a pepper plant containing in its genetic material one or more transgenes and to the transgenic pepper plant produced by those methods.

In another embodiment, the present invention is directed to single gene converted plants of hybrid pepper 'E20S1012777'. The single transferred gene may preferably be a dominant or recessive allele. Preferably, the single transferred gene will confer such trait as sex determination, herbicide resistance, insect resistance, resistance for bacterial, fungal, or viral disease, improved harvest characteristics, enhanced nutritional quality, or improved agronomic quality. The single gene may be a naturally occurring pepper gene or a transgene introduced through genetic engineering techniques.

In another embodiment, the present invention is directed to methods for developing pepper plants in a pepper plant breeding program using plant breeding techniques including recurrent selection, backcrossing, pedigree breeding, restriction fragment length polymorphism enhanced selection, genetic marker enhanced selection and transformation. Marker loci such as restriction fragment polymorphisms or random amplified DNA have been published for many years and may be used for selection (See, Pierce et al., *HortScience* (1990) 25:605-615; Wehner, T., *Cucurbit Genetics Cooperative Report*, (1997) 20: 66-88; and Kennard et al., *Theorical Applied Genetics* (1994) 89:217-224). Seeds, pepper plants, and parts thereof produced by such breeding methods are also part of the invention.

In addition to the exemplary aspects and embodiments described above, further aspects and embodiments will become apparent by reference by study of the following descriptions.

DETAILED DESCRIPTION OF THE INVENTION

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The selected germplasm is crossed in order to recombine the desired traits and through selection varieties or parent lines are developed. The goal is to combine in a single variety or hybrid an improved combination of desirable traits from the parental germplasm. These important traits may include higher yield, field performance, fruit and agronomic quality such as fruit shape and length, resistance to diseases and insects, and tolerance to drought and heat.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection. These processes, which lead to the final step of marketing and distribution, usually take from five to ten years from the time the first cross or selection is made.

One goal of pepper plant breeding is to develop new, unique and superior pepper cultivars. A breeder can initially select and cross two or more parental lines, followed by repeated selfing and selection, producing many new genetic combinations. Moreover, a breeder can generate multiple different genetic combinations by crossing, selfing, and mutations. A plant breeder can then select which germplasms to advance to the next generation. These germplasms may then be grown under different geographical, climatic, and soil conditions, and further selections can be made during, and at the end of, the growing season.

The development of commercial pepper cultivars thus requires the development of pepper parental lines, the crossing of these lines, and the evaluation of the crosses. Pedigree breeding and recurrent selection breeding methods are used to develop cultivars from breeding populations. Breeding programs combine desirable traits from two or more varieties or various broad-based sources into breeding pools from which lines are developed by selfing and selection of desired phenotypes. The new lines are crossed with other lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$s or by intercrossing two $F_1$s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding may be used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding may also be used introducing new traits into pepper varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company, 1993.

The production of double haploids can also be used for the development of homozygous lines in a breeding program. Double haploids are produced by the doubling of a set of chromosomes from a heterozygous plant to produce a completely homozygous individual. For example, see Wan, et al., *Theor. Appl. Genet.*, 77:889-892, 1989.

Additional non-limiting examples of breeding methods that may be used include, without limitation, those found in *Principles of Plant Breeding*, John Wiley and Son, pp. 115-161, 1960; Allard, 1960; Simmonds, 1979; Sneep et al., 1979; Fehr, 1987; "Carrots and Related Vegetable Umbelliferae", Rubatzky, V. E., et al., 1999.

DEFINITIONS

In the description and tables that follow, a number of terms are used. In order to provide a clear and consistent understanding of the specification and claims, including the scope to be given such terms, the following definitions are provided:

Allele. The allele is any of one or more alternative forms of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Covered cultivation. Any type of cultivation where the plants are not exposed to direct sunlight. The covering includes but is not limited to greenhouses, glasshouses, net-houses, plastic houses and tunnels.

Essentially all the physiological and morphological characteristics. A plant having essentially all the physiological and morphological characteristics means a plant having the physiological and morphological characteristics of the recurrent parent, except for the characteristics derived from the converted gene.

Fructose content. As used herein, "fructose content" refers to the quantity of fructose in a green pepper fruit in mg/kg of fresh weight.

Glucose content. As used herein, "glucose content" refers to the quantity of glucose in a green pepper fruit in mg/kg of fresh weight.

Green pepper plant. As used herein, a "green pepper plant" is a plant that is developed for the harvest of green pepper fruits.

Internode. An "internode" refers to the stem segment between nodes.

Pepper fruit. As used herein, a "pepper fruit" is a fruit produced by a *Capsicum annuum* plant and is commonly referred to as a bell pepper. The color of a pepper fruit can be green, red, yellow, orange and, more rarely, white, black, and brown, depending on when they are harvested and the specific cultivar. Green peppers are unripe bell peppers, while the others are all ripe, with the color variation based on cultivar selection.

Propagate. To "propagate" a plant means to reproduce the plant by means including, but not limited to, seeds, cuttings, divisions, tissue culture, embryo culture or other in vitro method.

Quantitative Trait Loci (QTL). As used herein, "quantitative trait loci" refers to genetic loci that control to some degree numerically representable traits that are usually continuously distributed.

Regeneration. As used herein, "regeneration" refers to the development of a plant from tissue culture.

Single gene converted. As used herein, "single gene converted" or "conversion plant" refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Transgene. As used herein, a "transgene" is a gene taken or copied from one organism and inserted into another organism. A transgene may be a gene that is foreign to the receiving organism or it may be a modified version of a native, or endogenous, gene.

Overview of the Hybrid Pepper Variety 'E20S1012777'

The taste of pepper fruit can vary with growing conditions and post-harvest storage treatment. In general, the sweetest pepper fruit are fruit allowed to ripen fully on the plant, while fruit harvested green are less sweet. Green peppers are unripe peppers, and typically, because they are unripe, green peppers are less sweet and slightly more bitter than yellow, orange, brown or red peppers.

Hybrid pepper 'E20S1012777' produces ripe fruit having a medium red color, and a short, moderately triangular shape. Fruit of the hybrid pepper 'E20S1012777' matures very early and can be grown in regions such as South Europe.

Additionally, hybrid pepper 'E20S1012777' has shown uniformity and stability for the traits, within the limits of environmental influence for the traits. Hybrid pepper 'E20S1012777' has been increased with continued observation for uniformity. No variant traits have been observed or are expected in 'E20S1012777'.

Objective Description of Hybrid Pepper 'E20S1012777'

Hybrid pepper variety 'E20S1012777' has the following morphologic and other characteristics:

General:
  Type: Mini-conical pepper
  Usage: Fresh market
  Type of culture: Open and protected cultivation (glasshouse and plastic house)
Plant:
  Seedling (anthocyanin coloration of hypocotyl): Present
  Shortened internode: Absent (Indeterminant)
  Height: Short
Fruit:
  Color before maturity: Green
  Intensity of color before maturity: Dark
  Length: Short (7.5 cm)
  Diameter: Narrow (4 cm)
  Predominant shape of longitudinal section: Moderately triangular
  Color at maturity: Red
  Intensity of color at maturity: Medium
  Predominant number of locules: Predominantly two
  Capsaicin in placenta: Absent
  Time of maturity: Very early
Disease/Pest Resistance:
  Tobamovirus pathotype $P_0$: Resistant
  Tobamovirus pathotype $P_1$: Resistant
  Tobamovirus pathotype $P_{1-2}$: Resistant
  Tobamovirus pathotype $P_{1-2-3}$: Susceptible
  Tomato Spotted Wilt Virus (TSWV) race P0: Susceptible Comparisons to Most Similar Variety Table 1 below compares some of the characteristics of hybrid pepper variety 'E20S1012777' with similar variety, 'E49.9523'. Column 1 lists the characteristics, column 2 shows the characteristics for hybrid pepper variety 'E20S1012777', and column 3 shows the characteristics for most similar pepper variety 'E49.9523'.

TABLE 1

| Characteristic | 'E20S1012777' | 'E49.9523' |
| --- | --- | --- |
| *Tobamovirus* pathotype $P_{1-2}$ Resistance | Resistant | Susceptible |
| Mature fruit color | Medium | Medium/Light |

Table 2 below compares some of the characteristics of hybrid pepper variety 'E20S1012777' with similar variety, 'E49.9524'. Column 1 lists the characteristics, column 2 shows the characteristics for hybrid pepper variety 'E20S1012777', and column 3 shows the characteristics for most similar pepper variety 'E49.9524'.

TABLE 2

| Characteristic | 'E20S1012777' | 'E49.9524' |
| --- | --- | --- |
| Fruit length | Longer | Shorter |
| Fruit diameter | Bigger | Smaller |
| Tobamovirus pathotype $P_{1-2}$ Resistance | Resistant | Susceptible |

Table 3 below compares some of the characteristics of hybrid pepper variety 'E20S1012777' with similar variety, 'E49.0264'. Column 1 lists the characteristics, column 2 shows the characteristics for hybrid pepper variety 'E20S1012777', and column 3 shows the characteristics for most similar pepper variety 'E49.0264'.

TABLE 3

| Characteristic | 'E20S1012777' | 'E49.0264' |
| --- | --- | --- |
| Plant height | Shorter | Taller |

Further Embodiments

This invention is also directed to methods for producing a pepper plant by crossing a first parent pepper plant with a second parent pepper plant, wherein the first or second pepper plant is the pepper plant 'E20S1012777'. Further, both first and second parent pepper plants may be 'E20S1012777'. Therefore, any methods using pepper hybrid 'E20S1012777' are part of this invention: selfing, backcrosses, hybrid breeding, and crosses to populations. Any plants produced using pepper hybrid 'E20S1012777' as at least one parent are within the scope of this invention.

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformed plants obtained with the protoplasm of the invention are intended to be within the scope of this invention.

This invention also is directed to methods for producing a pepper plant by crossing a first parent pepper plant with a second parent pepper plant wherein either the first or second parent pepper plant is a hybrid pepper plant of hybrid 'E20S1012777'. Further, both first and second parent pepper plants can come from the hybrid pepper 'E20S1012777'. All plants produced using hybrid pepper 'E20S1012777' as a parent are within the scope of this invention, including plants derived from hybrid pepper 'E20S1012777'.

As used herein, the term plant includes plant cells, plant protoplasts, plant cell tissue cultures from which pepper plants can be regenerated, plant calli, plant clumps and plant cells that are intact in plants or parts of plants, such as embryos, pollen, ovules, flowers, leaves, stems, and the like.

As it is well known in the art, tissue culture of pepper can be used for the in vitro regeneration of pepper plants. Tissues cultures of various tissues of pepper and regeneration of plants therefrom are well known and published. By way of example, tissue cultures, some comprising organs to be used to produce regenerated plants, have been described in Burza, et al., *Plant Breeding*. 1995, 114: 4, 341-345, Pellinen, *Angewandte Botanik*. 1997, 71: 3/4, 116-118, Kuijpers, et al., *Plant Cell Tissue and Organ Culture*. 1996, 46: 1, 81-83, Colijn-Hooymans, et al., *Plant Cell Tissue and Organ Culture*. 1994, 39: 3, 211-217, Lou, et al., *HortScience*. 1994, 29: 8, 906-909, Tabei, et al., *Breeding Science*. 1994, 44: 1, 47-51, Sarmanto, et al., *Plant Cell Tissue and Organ Culture* 31:3 185-193 (1992), Cade, et al., *Journal of the American Society for Horticultural Science* 115:4 691-696 (1990), Chee, et al., *HortScience* 25:7, 792-793 (1990), Kim, et al., HortScience 24:4 702 (1989), Punja, et al., *Plant Cell Report* 9:2 61-64 (1990). Pepper plants could be regenerated by somatic embryogenesis. It is clear from the literature that the state of the art is such that these methods of obtaining plants are "conventional" in the sense that they are routinely used and have a very high rate of success. Thus, another aspect of this invention is to provide cells which upon growth and differentiation produce pepper plants having the physiological and morphological characteristics of hybrid pepper 'E20S1012777'.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes." Over the last fifteen to twenty years several methods for producing transgenic plants have been developed, and the present invention, in particular embodiments, also relates to transformed versions of the claimed hybrid.

Plant transformation involves the construction of an expression vector that will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed pepper plants, using transformation methods as described below to incorporate transgenes into the genetic material of the pepper plant(s).

Expression Vectors for Pepper Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals which confers resistance to kanamycin (Fraley, et al., *Proc. Natl. Acad. Sci. U.S.A.,* 80:4803 (1983)). Another commonly used selectable marker gene is the hygromycin phosphotransferase gene which confers resistance to the antibiotic hygromycin (Vanden Elzen, et al., *Plant Mol. Biol.,* 5:299 (1985)).

Additional selectable marker genes of bacterial origin that confer resistance to antibiotics include gentamycin acetyl transferase, streptomycin phosphotransferase, aminoglycoside-3'-adenyl transferase, the bleomycin resistance determinant (Hayford, et al., *Plant Physiol.* 86:1216 (1988), Jones, et al., *Mol. Gen. Genet.,* 210:86 (1987), Svab, et al., *Plant Mol. Biol.* 14:197 (1990), Hille, et al., *Plant Mol. Biol.* 7:171 (1986)). Other selectable marker genes confer resistance to herbicides such as glyphosate, glufosinate or bromoxynil (Comai, et al., *Nature* 317:741-744 (1985), Gordon-Kamm, et al., *Plant Cell* 2:603-618 (1990) and Stalker, et al., *Science* 242:419-423 (1988)).

Selectable marker genes for plant transformation that are not of bacterial origin include, for example, mouse dihydrofolate reductase, plant 5-enolpyruvylshikimate-3-phosphate synthase and plant acetolactate synthase (Eichholtz, et al., *Somatic Cell Mol. Genet.* 13:67 (1987), Shah, et al., *Science* 233:478 (1986), Charest, et al., *Plant Cell Rep.* 8:643 (1990)).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include .alpha.-glucuronidase (GUS), α-galactosidase, luciferase and chloramphenicol, acetyltransferase (Jefferson, R. A., *Plant Mol. Biol. Rep.* 5:387 (1987), Teeri, et al., *EMBO J.* 8:343 (1989), Koncz, et al., *Proc. Natl. Acad. Sci. U.S.A.* 84:131 (1987), DeBlock, et al., *EMBO J.* 3:1681 (1984)).

In vivo methods for visualizing GUS activity that do not require destruction of plant tissues are available (Molecular Probes publication 2908, IMAGENE GREEN, pp. 1-4 (1993) and Naleway, et al., *J. Cell Biol.* 115:151a (1991)). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells (Chalfie, et al., *Science* 263:802 (1994)). GFP and mutants of GFP may be used as screenable markers.

Expression Vectors for Pepper Transformation: Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissue are referred to as "tissue-specific." A "cell type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in pepper. Optionally, the inducible promoter is operably linked to a nucleotide sequence encoding a signal sequence which is operably linked to a gene for expression in pepper. With an inducible promoter the rate of transcription increases in response to an inducing agent.

Any inducible promoter can be used in the instant invention. See, Ward, et al., *Plant Mol. Biol.* 22:361-366 (1993). Exemplary inducible promoters include, but are not limited to, that from the ACEI system which responds to copper (Meft, et al., *Proc. Natl. Acad. Sci. U.S.A.* 90:4567-4571 (1993)); In2 gene from maize which responds to benzenesulfonamide herbicide safeners (Hershey, et al., *Mol. Gen Genetics* 227:229-237 (1991) and Gatz, et al., *Mol. Gen. Genetics* 243:32-38 (1994)) or Tet repressor from Tn10 (Gatz, et al., *Mol. Gen. Genetics* 227:229-237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena, et al., *Proc. Natl. Acad. Sci. U.S.A.* 88:0421 (1991).

B. Constitutive Promoters

A constitutive promoter is operably linked to a gene for expression in pepper or the constitutive promoter is operably linked to a nucleotide sequence encoding a signal sequence which is operably linked to a gene for expression in pepper.

Many different constitutive promoters can be utilized in the instant invention.

Exemplary constitutive promoters include, but are not limited to, the promoters from plant viruses such as the 35S promoter from CaMV (Odell, et al., *Nature* 313:810-812 (1985) and the promoters from such genes as rice actin (McElroy, et al., *Plant Cell* 2:163-171 (1990)); ubiquitin (Christensen, et al., *Plant Mol. Biol.* 12:619-632 (1989) and Christensen, et al., *Plant Mol. Biol.* 18:675-689 (1992)); pEMU (Last, et al., *Theor. Appl. Genet.* 81:581-588 (1991)); MAS (Velten, et al., *EMBO J.* 3:2723-2730 (1984)) and maize H3 histone (Lepetit, et al., *Mol. Gen. Genetics* 231: 276-285 (1992) and Atanassova, et al., *Plant Journal* 2 (3): 291-300 (1992)). The ALS promoter, Xba1/Nco1 fragment 5' to the *Brassica napus* ALS3 structural gene (or a nucleotide sequence similarity to said Xba1/Nco1 fragment), represents a particularly useful constitutive promoter. See, PCT Application WO 96/30530.

C. Tissue-Specific or Tissue-Preferred Promoters

A tissue-specific promoter is operably linked to a gene for expression in pepper. Optionally, the tissue-specific promoter is operably linked to a nucleotide sequence encoding a signal sequence which is operably linked to a gene for expression in pepper. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai, et al., *Science* 23:476-482 (1983) and Sengupta-Gopalan, et al., *Proc. Natl. Acad. Sci. U.S.A.* 82:3320-3324 (1985)); a leaf-specific and light-induced promoter such as that from cab or rubisco (Simpson, et al., *EMBO J.* 4(11):2723-2729 (1985) and Timko, et al., *Nature* 318:579-582 (1985)); an anther-specific promoter such as that from LAT52 (Twell, et al., *Mol. Gen. Genetics* 217:240-245 (1989)); a pollen-specific promoter such as that from Zm13 (Guerrero, et al., *Mol. Gen. Genetics* 244:161-168 (1993)) or a microspore-preferred promoter such as that from apg (Twell, et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., *Plant Mol. Biol.* 20:49 (1992), Close, P. S., Master's Thesis, Iowa State University (1993), Knox, C., et al., "Structure and Organization of Two Divergent Alpha-Amylase Genes from Barley," *Plant Mol. Biol.* 9:3-17 (1987), Lerner, et al., *Plant Physiol.* 91:124-129 (1989), Fontes, et al., *Plant Cell* 3:483-496 (1991), Matsuoka, et al., *Proc. Natl. Acad. Sci.* 88:834 (1991), Gould, et al., *J. Cell. Biol.* 108:1657 (1989), Creissen, et al., *Plant J.* 2:129 (1991), Kalderon, et al., A short amino acid sequence able to specify nuclear location, *Cell* 39:499-509 (1984), Steifel, et al., Expression of a maize cell wall hydroxyproline-rich glycoprotein gene in early leaf and root vascular differentiation, *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is pepper. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see *Methods in Plant Molecular Biology and Biotechnology*, Glick and Thompson Eds., CRC Press, Inc., Boca Raton, pp. 269-284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See, for example, Jones, et al., *Science* 266:789 (1994) (cloning of the tomato Cf-9 gene for resistance to *Cladosporium flavum*); Martin, et al., *Science* 262:1432 (1993) (tomato Pto gene for resistance to *Pseudomonas syringae* pv. tomato encodes a protein kinase); Mindrinos, et al., *Cell* 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser, et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclosure by Van Damme, et al., *Plant Molec. Biol.* 24:25 (1994), who disclose the nucleotide sequences of several *Clivia miniata* mannose-binding lectin genes.

D. A vitamin-binding protein such as avidin. See, PCT Application US 93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe, et al., *J. Biol. Chem.* 262:16793 (1987) (nucleotide sequence of rice cysteine proteinase inhibitor), Huub, et al., *Plant Molec. Biol.* 21:985 (1993) (nucleotide sequence of cDNA encoding tobacco proteinase inhibitor I), Sumitani, et al., *Biosci. Biotech. Biochem.* 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock, et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt, et al., *Biochem. Biophys. Res. Comm.* 163:1243 (1989) (an allostatin is identified in *Diploptera puntata*). See also, U.S. Pat. No. 5,266,317 to Tomalski, et al., who disclose genes encoding insect-specific, paralytic neurotoxins.

H. An insect-specific venom produced in nature by a snake, a wasp, etc. For example, see Pang, et al., *Gene* 116:165 (1992), for disclosure of heterologous expression in plants of a gene coding for a scorpion insectotoxic peptide.

I. An enzyme responsible for a hyper-accumulation of a monoterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See, PCT Application WO 93/02197 in the name of Scott, et al., which discloses the nucleotide sequence of a callase gene. DNA molecules which contain chitinase-encoding sequences can be obtained, for example, from the ATCC under Accession Nos. 39637 and 67152. See also, Kramer, et al., *Insect Biochem. Molec. Biol.* 23:691 (1993), who teach the nucleotide sequence of a cDNA encoding tobacco hornworm chitinase, and Kawalleck, et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella, et al., *Plant Molec. Biol.* 24:757 (1994), of nucleotide sequences for mung bean calmodulin cDNA clones, and Griess, et al., *Plant Physiol.* 104:1467 (1994), who provide the nucleotide sequence of a maize calmodulin cDNA clone.

L. A hydrophobic moment peptide. See, PCT Application WO 95/16776 (disclosure of peptide derivatives of tachyplesin which inhibit fungal plant pathogens) and PCT Application WO 95/18855 (teaches synthetic antimicrobial peptides that confer disease resistance), the respective contents of which are hereby incorporated by reference.

M. A membrane permease, a channel former or a channel blocker. For example, see the disclosure of Jaynes, et al., *Plant Sci* 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. See, Taylor, et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki, et al., *Nature* 366:469 (1993), who show that transgenic plants expressing recombinant antibody genes are protected from virus attack.

Q. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See, Lamb, et al., *Bio/Technology* 10:1436 (1992). The cloning and characterization of a gene which encodes a bean endopolygalacturonase-inhibiting protein is described by Toubart, et al., *Plant J.* 2:367 (1992).

R. A developmental-arrestive protein produced in nature by a plant. For example, Logemann, et al., *Bio/Technology* 10:305 (1992), have shown that transgenic plants expressing the barley ribosome-inactivating gene have an increased resistance to fungal disease.

2. Genes that Confer Resistance to an Herbicide:

A. An herbicide that inhibits the growing point or meristem, such as an imidazolinone or a sulfonylurea. Exemplary genes in this category code for mutant ALS and AHAS enzyme as described, for example, by Lee, et al., *EMBO J.* 7:1241 (1988), and Miki, et al., *Theor. Appl. Genet.* 80:449 (1990), respectively.

B. Glyphosate (resistance conferred by mutant 5-enolpyruvlshikimate-3-phosphate synthase (EPSPS) and aroA genes, respectively) and other phosphono compounds such as glufosinate (phosphinothricin acetyl transferase (PAT) and *Streptomyces hygroscopicus* phosphinothricin-acetyl transferase PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC Accession No. 39256, and the nucleotide sequence of the mutant gene is disclosed in U.S. Pat. No. 4,769,061 to Comai. See also, Umaballava-Mobapathie in *Transgenic Research.* 1999, 8: 1, 33-44 that discloses *Lactuca sativa* resistant to glufosinate. European Patent Application No. 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in European Patent Application No. 0 242 246 to Leemans, et al., DeGreef, et al., *Bio/Technology* 7:61 (1989), describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Accl-S1, Accl-S2 and Accl-S3 genes described by Marshall, et al., *Theor. Appl. Genet.* 83:435 (1992).

C. An herbicide that inhibits photosynthesis, such as a triazine (psbA and gs+ genes) and a benzonitrile (nitrilase gene). Przibilla, et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes, et al., *Biochem. J.* 285:173 (1992).

D. Acetohydroxy acid synthase, which has been found to make plants that express this enzyme resistant to multiple types of herbicides, has been introduced into a variety of plants. See, Hattori, et al., *Mol. Gen. Genet.* 246:419, 1995. Other genes that confer tolerance to herbicides include a gene encoding a chimeric protein of rat cytochrome P4507A1 and yeast NADPH-cytochrome P450 oxidoreductase (Shiota, et al., *Plant Physiol.*, 106:17, 1994), genes for glutathione reductase and superoxide dismutase (Aono, et al., *Plant Cell Physiol.* 36:1687, 1995), and genes for various phosphotransferases (Datta, et al., *Plant Mol. Biol.* 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and International Publication WO 01/12825.

3. Genes that Confer or Contribute to a Value-Added Trait, Such as:

A. Increased iron content of the pepper, for example, by transforming a plant with a soybean ferritin gene as described in Goto, et al., *Acta Horticulturae.* 2000, 521, 101-109.

B. Increased sweetness of the pepper by transferring a gene coding for monellin that elicits a flavor 100,000 times sweeter than sugar on a molar basis. See, Penarrubia, et al., *Biotechnology.* 1992, 10: 561-564.

4. Genes that Control Male-Sterility:

A. Introduction of a deacetylase gene under the control of a tapetum-specific promoter and with the application of the chemical N-Ac-PPT. See, International Publication WO 01/29237.

B. Introduction of various stamen-specific promoters. See, International Publications WO 92/13956 and WO 92/13957.

C. Introduction of the barnase and the barstar genes. See, Paul, et al., *Plant Mol. Biol.* 19:611-622, 1992).

Methods for Pepper Transformation

Numerous methods for plant transformation have been developed, including biological and physical, plant transformation protocols. See, for example, Miki, et al., "Procedures for Introducing Foreign DNA into Plants" in *Methods in Plant Molecular Biology and Biotechnology*, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in *Methods in Plant Molecular Biology and Biotechnology*, Glick and Thompson Eds., CRC Press, Inc., Boca Raton, pp. 89-119 (1993).

A. *Agrobacterium*-Mediated Transformation

One method for introducing an expression vector into plants is based on the natural transformation system of *Agrobacterium*. See, for example, Horsch, et al., *Science* 227:1229 (1985), Curtis, et al., *Journal of Experimental Botany.* 1994, 45: 279, 1441-1449, Tones, et al., *Plant Cell Tissue and Organic Culture.* 1993, 34: 3, 279-285, Dinant, et al., *Molecular Breeding.* 1997, 3: 1, 75-86. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Reports* 8:238 (1989). See also, U.S. Pat. No. 5,591,616 issued Jan. 7, 1997.

B. Direct Gene Transfer

Several methods of plant transformation collectively referred to as direct gene transfer have been developed as an alternative to *Agrobacterium*-mediated transformation. A generally applicable method of plant transformation is microprojectile-mediated transformation wherein DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Russell, D. R., et al. *Pl. Cell. Rep.* 12(3, January), 165-169 (1993), Aragao, F. J. L., et al. *Plant Mol. Biol.* 20(2, October), 357-359 (1992), Aragao, F. J. L., et al. *Pl. Cell. Rep.* 12(9, July), 483-490 (1993). Aragao, *Theor. Appl. Genet.* 93: 142-150 (1996), Kim, J.; Minamikawa, T. Plant *Science* 117: 131-138 (1996), Sanford, et al., *Part. Sci. Technol.* 5:27 (1987), Sanford, J. C., *Trends Biotech.* 6:299 (1988), Klein, et al., *Bio/Technology* 6:559-563 (1988), Sanford, J. C., *Physiol Plant* 7:206 (1990), Klein, et al., *Biotechnology* 10:268 (1992).

Another method for physical delivery of DNA to plants is sonication of target cells. Zhang, et al., *Bio/Technology* 9:996 (1991). Alternatively, liposome and spheroplast fusion have been used to introduce expression vectors into plants. Deshayes, et al., *EMBO J.*, 4:2731 (1985), Christou, et al., *Proc Natl. Acad. Sci. U.S.A.* 84:3962 (1987). Direct uptake of DNA into protoplasts using $CaCl_2$ precipitation, polyvinyl alcohol or poly-L-ornithine has also been reported. Hain, et al., *Mol. Gen. Genet.* 199:161 (1985) and Draper, et al., *Plant Cell Physiol.* 23:451 (1982). Electroporation of protoplasts and whole cells and tissues have also been described. Saker, M.; Kuhne, T *Biologia Plantarum* 40(4): 507-514 (1997/98), Donn, et al., In Abstracts of VIIth International Congress on Plant Cell and Tissue Culture IAPTC, A2-38, p. 53 (1990); D'Halluin, et al., *Plant Cell* 4:1495-1505 (1992) and Spencer, et al., *Plant Mol. Biol.* 24:51-61 (1994). See also, Chupean, et al., *Biotechnology.* 1989, 7: 5, 503-508.

Following transformation of pepper target tissues, expression of the above-described selectable marker genes allows for preferential selection of transformed cells, tissues and/or plants, using regeneration and selection methods now well known in the art.

The foregoing methods for transformation would typically be used for producing a transgenic line. The transgenic line could then be crossed, with another (non-transformed or transformed) line, in order to produce a new transgenic pepper line. Alternatively, a genetic trait which has been engineered into a particular pepper cultivar using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

Genetic Marker Profile Through SSR and First Generation Progeny

In addition to phenotypic observations, a plant can also be identified by its genotype. The genotype of a plant can be characterized through a genetic marker profile which can identify plants of the same variety or a related variety or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Cregan et al., "An Integrated Genetic Linkage Map of the Soybean Genome" *Crop Science* 39:1464-1490 (1999), and Berry et al., "Assessing Probability of Ancestry Using Simple Sequence Repeat Profiles: Applications to Maize Inbred Lines and Soybean Varieties" *Genetics* 165:331-342 (2003), each of which are incorporated by reference herein in their entirety.

Particular markers used for these purposes are not limited to any particular set of markers, but are envisioned to include any type of marker and marker profile which provides a means of distinguishing varieties. One method of comparison is to use only homozygous loci for hybrid pepper 'E20S1012777'.

Primers and PCR protocols for assaying these and other markers are disclosed in the Soybase (sponsored by the USDA Agricultural Research Service and Iowa State University). In addition to being used for identification of hybrid pepper 'E20S1012777' and plant parts and plant cells of variety hybrid pepper 'E20S1012777', the genetic profile may be used to identify a pepper plant produced through the use of hybrid pepper 'E20S1012777' or to verify a pedigree for progeny plants produced through the use of hybrid pepper 'E20S1012777'. The genetic marker profile is also useful in breeding and developing backcross conversions.

The present invention comprises a pepper plant characterized by molecular and physiological data obtained from the representative sample of said variety deposited with the American Type Culture Collection (ATCC). Further provided by the invention is a pepper plant formed by the combination of the disclosed pepper plant or plant cell with another pepper plant or cell and comprising the homozygous alleles of the variety.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. See for example, Gong, L., et al., "Microsatellites for the genus *Cucurbita* and an SSR-based genetic linkage map of *Cucurbita pepo* L." *Theor Appl Genet.* (June 2008) 117(1): 37-48. Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology. Microsatellites for the genus *Cucurbita* and an SSR-based genetic linkage map of *Cucurbita pepo*.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties it is preferable if all SSR profiles are performed in the same lab.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for pepper plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wun1, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the pepper lines of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a pepper plant according to the invention. Non-limiting examples of particular genes and corresponding phenotypes one may choose to introduce into a pepper plant include one or more genes for insect tolerance, such as a *Bacillus thuringiensis* (Bt) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

Single-Gene Conversions

When the terms pepper plant, hybrid, cultivar or pepper line are used in the context of the present invention, this also includes any single gene conversions. The term "single gene converted plant" as used herein refers to those pepper plants which are developed by a plant breeding technique called backcrossing wherein essentially all of the desired morphological and physiological characteristics of a cultivar are recovered in addition to the single gene transferred into the line via the backcrossing technique. Backcrossing methods can be used with the present invention to improve or introduce a characteristic into the line. The term "backcrossing" as used herein refers to the repeated crossing of a hybrid progeny back to one of the parental pepper plants for that line, backcrossing 1, 2, 3, 4, 5, 6, 7, 8, or more times to the recurrent parent. The parental pepper plant which contributes the gene for the desired characteristic is termed the nonrecurrent or donor parent. This terminology refers to the fact that the nonrecurrent parent is used one time in the backcross protocol and therefore does not recur. The parental pepper plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original cultivar of interest (recurrent parent) is crossed to a second line (nonrecurrent parent) that carries the single gene of interest to be transferred. The resulting progeny from this cross are then crossed again to the recurrent parent and the process is repeated until a pepper plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original line. To accomplish this, a single gene of the recurrent cultivar is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new line but that can be improved by backcrossing techniques. Single gene traits may or may not be transgenic, examples of these traits include but are not limited to, male sterility, modified fatty acid metabolism, modified carbohydrate metabolism, herbicide resistance, nematode resistance, resistance for bacterial, fungal, or viral disease, insect resistance, enhanced nutritional quality, industrial usage, yield stability and yield enhancement. These genes are generally inherited through the nucleus. Several of these single gene traits are described in U.S. Pat. Nos. 5,777,196, 5,948,957 and 5,969,212, the disclosures of which are specifically hereby incorporated by reference.

Tissue Culture

Further reproduction of the variety can occur by tissue culture and regeneration. Tissue culture of various tissues of pepper and regeneration of plants therefrom is well known and widely published. For example, reference may be had to Teng, et al., *HortScience*. 1992, 27: 9, 1030-1032 Teng, et al., *HortScience*. 1993, 28: 6, 669-1671, Zhang, et al., *Journal of Genetics and Breeding*. 1992, 46: 3, 287-290, Webb, et al., *Plant Cell Tissue and Organ Culture*. 1994, 38: 1, 77-79, Curtis, et al., *Journal of Experimental Botany*. 1994, 45: 279, 1441-1449, Nagata, et al., *Journal for the American Society for Horticultural Science*. 2000, 125: 6, 669-672, and Ibrahim, et al., *Plant Cell, Tissue and Organ Culture*. (1992), 28(2): 139-145. It is clear from the literature that the state of the art is such that these methods of obtaining plants are routinely used and have a very high rate of success. Thus, another aspect of this invention is to provide cells which upon growth and differentiation produce pepper plants having the physiological and morphological characteristics of the hybrid 'E20S1012777'.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

Additional Breeding Methods

This invention also is directed to methods for producing a pepper plant by crossing a first parent pepper plant with a second parent pepper plant wherein the first or second parent pepper plant is a pepper plant of hybrid 'E20S1012777'. Further, both first and second parent pepper plants can come from pepper hybrid 'E20S1012777'. Thus, any such methods using pepper hybrid 'E20S1012777' are part of this invention: selfing, backcrosses, hybrid production, crosses to populations, and the like. All plants produced using pepper hybrid 'E20S1012777' as at least one parent are within the scope of this invention, including those developed from cultivars derived from pepper hybrid 'E20S1012777'. Advantageously, this pepper cultivar could be used in crosses with other, different, pepper plants to produce the first generation ($F_1$) pepper hybrid seeds and plants with superior characteristics. The cultivar of the invention can also be used for transformation where exogenous genes are introduced and expressed by the cultivar of the invention. Genetic variants created either through traditional breeding methods using pepper hybrid 'E20S1012777' or through transformation of hybrid 'E20S1012777' by any of a number of protocols known to those of skill in the art are intended to be within the scope of this invention.

The following describes breeding methods that may be used with pepper hybrid 'E20S1012777' in the development of further pepper plants. One such embodiment is a method for developing progeny pepper plants in a pepper plant breeding program comprising: obtaining the pepper plant, or a part thereof, of hybrid 'E20S1012777', utilizing said plant or plant part as a source of breeding material, and selecting a pepper hybrid 'E20S1012777' progeny plant with molecular markers in common with hybrid 'E20S1012777' and/or with morphological and/or physiological characteristics selected from the characteristics listed above. Breeding steps that may be used in the pepper plant breeding program include pedigree breeding, backcrossing, mutation breeding, and recurrent selection. In conjunction with these steps, techniques such as RFLP-enhanced selection, genetic marker enhanced selection (for example, SSR markers) and the making of double haploids may be utilized.

Another method involves producing a population of pepper hybrid 'E20S1012777' progeny pepper plants, by crossing hybrid 'E20S1012777' with another pepper plant, thereby producing a population of pepper plants, which, on average, derive 50% of their alleles from pepper hybrid 'E20S1012777'. A plant of this population may be selected and repeatedly selfed or sibbed with a pepper plant resulting from these successive filial generations. One embodiment of this invention is the pepper cultivar produced by this method and that has obtained at least 50% of its alleles from pepper hybrid 'E20S1012777'.

Additional methods include, without limitation, chasing selfs. Chasing selfs involves identifying inbred plants among pepper plants that have been grown from hybrid pepper seed. Once the seed is planted, the inbred plants may be identified and selected due to their decreased vigor relative to the hybrid plants that grow from the hybrid seed. By locating the inbred plants, isolating them from the rest of the plants, and self-pollinating them (i.e., "chasing selfs"), a breeder can obtain an inbred line that is identical to an inbred parent used to produce the hybrid.

Accordingly, another aspect of the present invention relates a method for producing an inbred pepper variety by: planting seed of the pepper variety 'E20S1012777'; growing plants from the seed; identifying one or more inbred pepper plants; controlling pollination in a manner which preserves homozygosity of the one or more inbred plants; and harvesting resultant seed from the one or more inbred plants. The step of identifying the one or more inbred pepper plants may further include identifying plants with decreased vigor, i.e., plants that appear less robust than plants of the pepper variety 'E20S1012777'. Pepper plants capable of expressing substantially all of the physiological and morphological characteristics of the parental inbred lines of pepper variety 'E20S1012777' include pepper plants obtained by chasing selfs from seed of pepper variety 'E20S1012777'.

One of ordinary skill in the art will recognize that once a breeder has obtained inbred pepper plants by chasing selfs from seed of pepper variety 'E20S1012777', the breeder can then produce new inbred plants such as by sib-pollinating, or by crossing one of the identified inbred pepper plant with a plant of the pepper variety 'E20S1012777'.

One of ordinary skill in the art of plant breeding would know how to evaluate the traits of two plant varieties to determine if there is no significant difference between the two traits expressed by those varieties. For example, see Fehr and Walt, *Principles of Cultivar Development*, pp. 261-286 (1987). Thus the invention includes pepper hybrid 'E20S1012777' progeny pepper plants comprising a combination of at least two hybrid 'E20S1012777' traits selected from the group consisting of those listed above or the hybrid 'E20S1012777' combination of traits listed in the Summary of the Invention, so that said progeny pepper plant is not significantly different for said traits than pepper hybrid 'E20S1012777' as determined at the 5% significance level when grown in the same environmental conditions. Using techniques described herein, molecular markers may be used to identify said progeny plant as a pepper hybrid 'E20S1012777' progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of pepper hybrid 'E20S1012777' may also be characterized through their filial relationship with pepper hybrid 'E20S1012777', as for example, being within a certain number of breeding crosses of pepper hybrid 'E20S1012777'. A breeding cross is a cross made to introduce new genetics into the progeny, and is distinguished from a cross, such as a self or a sib cross, made to select among existing genetic alleles. The lower the number of breeding crosses in the pedigree, the closer the relationship between pepper hybrid 'E20S1012777' and its progeny. For example, progeny produced by the methods described herein may be within 1, 2, 3, 4, or 5 breeding crosses of pepper hybrid 'E20S1012777'.

As used herein, the term "plant" includes plant cells, plant protoplasts, plant cell tissue cultures from which pepper plants can be regenerated, plant calli, plant clumps and plant cells that are intact in plants or parts of plants, such as fruit, leaves, pollen, embryos, cotyledons, hypocotyl, roots, root tips, anthers, pistils, flowers, seeds, stems and the like.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

DEPOSIT INFORMATION

A deposit of the hybrid pepper 'E20S1012777' is maintained by Enza Zaden USA, Inc., having an address at 7 Harris Place, Salinas, Calif. 93901, United States. Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of hybrid pepper 'E20S1012777' were deposited on Jun. 13, 2016 according to the Budapest Treaty in the National Collection of Industrial, Food and Marine Bacteria Ltd (NCIMB Ltd), Ferguson Building, Craibstone Estate, Bucksburn, Aberdeen, AB21 9YA, United Kingdom. The deposit has been assigned NCIMB number 42587. Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

The invention claimed is:

1. Hybrid *Capsicum annuum* pepper seed designated as 'E20S1012777', representative sample of seed having been deposited under NCIMB Accession Number 42587.

2. A pepper plant produced by growing the seed of claim 1.

3. A plant part from the plant of claim 2, wherein said part is a leaf, a fruit, or a cell.

4. A *Capsicum annuum* pepper plant having all the physiological and morphological characteristics of the pepper plant of claim 2.

5. A plant part from the plant of claim 4, wherein said part is a leaf, a fruit, or a cell.

6. Pollen or an ovule of the plant of claim 2.

7. A protoplast produced from the plant of claim 2.

8. A tissue culture produced from protoplasts or cells from the plant of claim 2, wherein said cells or protoplasts are produced from a plant part selected from the group consisting of leaf, anther, pistil, stem, petiole, root, root tip, fruit, seed, flower, cotyledon, hypocotyl, embryo, and meristematic cell.

9. A pepper plant regenerated from the tissue culture of claim 8, wherein the plant has all of the morphological and physiological characteristics of a *Capsicum annuum* pepper plant produced by growing seed designated as 'E20S1012777', representative sample of seed having been deposited under NCIMB Accession Number 42587.

10. A method of making pepper seeds, said method comprising crossing the plant of claim 2 with another *Capsicum annuum* pepper plant and harvesting seed therefrom.

11. The plant part of claim 3, wherein said part is a fruit.

12. The plant part of claim 5, wherein said part is a fruit.

* * * * *